United States Patent
Berner et al.

(10) Patent No.: US 6,233,471 B1
(45) Date of Patent: May 15, 2001

(54) SIGNAL PROCESSING FOR MEASUREMENT OF PHYSIOLOGICAL ANALYSIS

(75) Inventors: Bret Berner, El Granada; Timothy C. Dunn, Menlo Park; Kathleen C. Farinas, San Carlos, all of CA (US); Michael D. Garrison, Seattle, WA (US); Ronald T. Kurnik, Foster City, CA (US); Matthew J. Lesho, San Mateo, CA (US); Russell O. Potts, San Francisco, CA (US); Janet A. Tamada, Mountain View, CA (US); Michael J. Tierney, San Jose, CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

(21) Appl. No.: 09/309,728

(22) Filed: May 11, 1999

Related U.S. Application Data

(60) Provisional application No. 60/085,344, filed on May 13, 1998.

(51) Int. Cl.[7] .......................................... A61B 5/05
(52) U.S. Cl. .................... 600/345; 600/346; 600/347; 600/309; 600/365
(58) Field of Search ................... 600/345, 309, 600/346, 347, 365

(56) References Cited

U.S. PATENT DOCUMENTS

| | | |
|---|---|---|
| 4,975,581 | 12/1990 | Robinson et al. . |
| 5,036,861 | 8/1991 | Sembrowich et al. . |
| 5,076,273 | 12/1991 | Schoendorfer et al. . |
| 5,086,229 | 2/1992 | Rosenthal et al. . |
| 5,139,023 | 8/1992 | Stanley et al. . |
| 5,140,985 | 8/1992 | Schroeder et al. . |
| 5,267,152 | 11/1993 | Yang et al. . |
| 5,279,543 | 1/1994 | Glikfeld et al. . |
| 5,362,307 | 11/1994 | Guy et al. . |
| 5,443,080 | 8/1995 | K'Angelo et al. . |
| 5,448,992 | * 9/1995 | Kupershmidt ................. 600/345 |
| 5,722,397 | * 3/1998 | Eppstein ........................ 600/345 |
| 5,730,714 | 3/1998 | Guy et al. . |
| 5,735,273 | 4/1998 | Kurnik et al. . |
| 5,752,512 | * 5/1998 | Gozani ........................... 600/345 |
| 5,771,890 | 6/1998 | Tamada . |
| 5,827,183 | 10/1998 | Kurnik et al. . |
| 6,014,577 | * 1/2000 | Henning et al. ................ 600/345 |
| 6,021,339 | * 2/2000 | Saito et al. .................... 600/345 |
| 6,023,629 | * 2/2000 | Tamada ......................... 600/347 |
| 6,144,869 | * 11/2000 | Berner et al. .................. 600/347 |

FOREIGN PATENT DOCUMENTS

| | | |
|---|---|---|
| WO 95/02357 | 1/1995 | (WO) . |
| WO 96/00109 | 1/1996 | (WO) . |
| WO 96/00110 | 1/1996 | (WO) . |
| WO 97/24059 | 7/1997 | (WO) . |
| WO 98/00194 | 1/1998 | (WO) . |

OTHER PUBLICATIONS

The Diabetes Control and Complications Trial Research, *New England J. Med.* 329:977–1036 (1993).

* cited by examiner

Primary Examiner—Cary O'Connor
Assistant Examiner—Navin Natnithithadha
(74) Attorney, Agent, or Firm—Barbara G. McClung; Robins & Associates

(57) ABSTRACT

A method is provided for continually or continuously measuring the concentration of target chemical analytes present in a biological system, and processing analyte-specific signals to obtain a measurement value that is closely correlated with the concentration of the target chemical analyte in the biological system. One important application of the invention involves a method for signal processing in a system for monitoring blood glucose values.

44 Claims, 3 Drawing Sheets

SIGNAL PROCESSING FOR MEASUREMENT OF PHYSIOLOGICAL ANALYSIS

CROSS-REFERENCE TO RELATED APPLICATION

This application is related to provisional patent application Ser. No. 60/085,344, filed May 13, 1998, from which priority is claimed under 35 USC §119(e) (1) and which application is incorporated herein by reference in its entirety.

FIELD OF THE INVENTION

The invention relates generally to methods for continually or continuously measuring the concentration of target chemical analytes present in a biological system. More particularly, the invention relates to methods for processing signals obtained during measurement of physiological analytes. One important application of the invention involves a method for monitoring blood glucose concentrations.

BACKGROUND OF THE INVENTION

A number of diagnostic tests are routinely performed on humans to evaluate the amount or existence of substances present in blood or other body fluids. These diagnostic tests typically rely on physiological fluid samples removed from a subject, either using a syringe or by pricking the skin. One particular diagnostic test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by fingerprick) for each test, and a determination of the glucose level using an instrument that reads glucose concentrations by electrochemical or colorimetric methods. Type I diabetics must obtain several fingerprick blood glucose measurements each day in order to maintain tight glycemic control. However, the pain and inconvenience associated with this blood sampling, along with the fear of hypoglycemia, has led to poor patient compliance, despite strong evidence that tight control dramatically reduces long-term diabetic complications. In fact, these considerations can often lead to an abatement of the monitoring process by the diabetic. See, e.g., The Diabetes Control and Complications Trial Research Group (1993) *New Engl. J. Med.* 0329:977–1036.

Recently, various methods for determining the concentration of blood analytes without drawing blood have been developed. For example, U.S. Pat. No. 5,267,152 to Yang et al. describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al.

U.S. Pat. Nos. 5,139,023 to Stanley et al., and U.S. Pat. No. 5,443,080 to D'Angelo et al. describe transdermal blood glucose monitoring devices that rely on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder.

In addition, U.S. Pat. No. 5,279,543 to Glikfeld et al. describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Finally, International Publication No. WO 96/00110, published Jan. 4, 1996, describes an iontophoretic apparatus for transdermal monitoring of a target substance, wherein an iontophoretic electrode is used to move an analyte into a collection reservoir and a biosensor is used to detect the target analyte present in the reservoir.

SUMMARY OF THE INVENTION

The present invention provides a method for continually or continuously measuring the concentration of an analyte present in a biological system. The method entails continually or continuously detecting an analyte from the biological system and deriving a raw signal therefrom, wherein the raw signal is related to the analyte concentration. A number of signal processing steps are then carried out in order to convert the raw signal into an initial signal output that is indicative of an analyte amount. The converted signal is then further converted into a value indicative of the concentration of analyte present in the biological system.

The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the raw signal including, but not limited to, physical, chemical, electrochemical, photochemical, spectrophotometric, polarimetric, colorimetric, radiometric, or like elements. In preferred embodiments of the invention, a biosensor is used which comprises an electrochemical sensing element.

In one particular embodiment of the invention, the raw signal is obtained using a transdermal sampling system that is placed in operative contact with a skin or mucosal surface of the biological system. The sampling system transdermally extracts the analyte from the biological system using any appropriate sampling technique, for example, iontophoresis.

The transdermal sampling system is maintained in operative contact with the skin or mucosal surface of the biological system to provide for such continual or continuous analyte measurement.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents, electrolytes, physiological analytes of interest (e.g., calcium, potassium, sodium, chloride, bicarbonate ($CO_2$), glucose, urea (blood urea nitrogen), lactate, hematocrit, and hemoglobin), lipids, and the like. In preferred embodiments, the analyte is a physiological analyte of interest, for example glucose, or a chemical that has a physiological action, for example a drug or pharmacological agent.

Accordingly, it is an object of the invention to provide a method for continually or continuously measuring an analyte present in a biological system, wherein raw signals are obtained from a suitable sensing apparatus, and then subjected to signal processing techniques. More particularly, the raw signals undergo a data screening method in order to eliminate outlier signals and/or poor (incorrect) signals using a predefined set of selection criteria. In addition, or alternatively, the raw signal can be converted in a conversion step which (i) removes or corrects for background information, (ii) integrates the raw signal over a sensing time period, (iii) performs any process which converts the raw signal from one signal type to another, or (iv) performs any combination of steps (i), (ii) and/or (iii). In preferred embodiments, the conversion step entails a baseline background subtraction method to remove background from the raw signal and an integration step. In other embodiments, the conversion step can be tailored for use with a sensing device that provides both active and reference (blank) signals; wherein mathematical transformations are used to individually smooth active and reference signals, and/or to subtract a weighted reference (blank) signal from the active signal. In still further embodiments, the conversion step includes correction functions which account for changing conditions in the biological system and/or the biosensor system (e.g., temperature fluctuations in the biological system, temperature fluctuations in the sensor element, skin conductivity fluctuations, or combinations thereof). The result of the conversion step is an initial signal output which provides a value which can be correlated with the concentration of the target analyte in the biological sample.

It is also an object of the invention to provide a signal processing calibration step, wherein the raw or initial signals obtained as described above are converted into an analyte-specific value of known units to provide an interpretation of the signal obtained from the sensing device. The interpretation uses a mathematical transformation to model the relationship between a measured response in the sensing device and a corresponding analyte-specific value. Such mathematical transformations can entail the use of linear or nonlinear regressions, or neural network algorithms. In one embodiment, the calibration step entails calibrating the sensing device using a single- or multi-point calibration, and then converting post-calibration data using correlation factors, time corrections and constants to obtain an analyte-specific value. Further signal processing can be used to refine the information obtained in the calibration step, for example, where a signal processing step is used to correct for signal differences due to variable conditions unique to the sensor element used to obtain the raw signal. In one embodiment, this further step is used to correct for signal time-dependence, particularly signal decline. In another embodiment, a constant offset term is obtained, which offset is added to the signal to account for a non-zero signal at an estimated zero analyte concentration.

Further, the methods of the present invention include enhancement of skin permeability by pricking the skin with micro-needles. In addition, the sampling system can be programed to begin execution of sampling and sensing at a defined time(s).

It is yet a further object of the invention to provide a monitoring system for continually or continuously measuring an analyte present in a biological system. The monitoring system comprises, in operative combination: (a) a sampling means for continually or continuously extracting the analyte from the biological system, (b) a sensing means in operative contact with the analyte extracted by the sampling means, and (c) a microprocessor means in operative communication with the sensing means. The sampling means is adapted for extracting the analyte across a skin or mucosal surface of a biological system. The sensing means is used to obtain a raw signal from the extracted analyte, wherein the raw signal is specifically related to the analyte. The microprocessor means is used to subject the raw signal to a conversion step, thereby converting the same into an initial signal output which is indicative of the amount of analyte extracted by the sampling means, and then perform a calibration step which correlates the initial signal output with a measurement value indicative of the concentration of analyte present in the biological system at the time of extraction. In one embodiment, the monitoring system uses iontophoresis to extract the analyte from the biological system. In other embodiments, the monitoring system is used to extract a glucose analyte from the biological system. Further, the microprocessor can be programed to begin execution of sampling and sensing at a defined time(s).

Additional objects, advantages and novel features of the invention will be set forth in part in the description which follows, and in part will become apparent to those skilled in the art upon examination of the following, or may be learned by practice of the invention.

DETAILED DESCRIPTION OF THE PREFERRED EMBODIMENTS

Figure 1A:
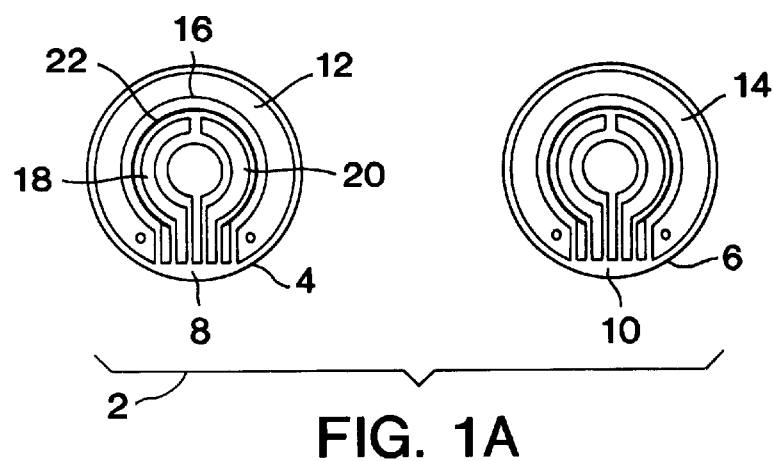
FIG. 1A depicts a top plan view of an iontophoretic collection reservoir and electrode assembly for use in a transdermal sampling device constructed according to the present invention.

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a time-dependent variable" includes a mixture of two or more such variables, reference to "an electrochemically active species" includes two or more such species, reference to "an analyte" includes mixtures of analytes, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

Definitions

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) *Nature* 214:986–988), and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (*Analytical Chemistry* 67(24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoir" and "collection insert" are used to describe any suitable containment means for containing a sample extracted from a biological system. The reservoir can include a material which is tonically conductive (e.g., water with ions therein), wherein another material such as a sponge-like material or hydrophilic polymer is used to keep the water in place. Such collection reservoirs can be in the form of a hydrogel (for example, in the shape of a disk or pad). Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives.

A "collection assembly", as used herein, refers to structures comprised of several layers, where the assembly includes at least one collection insert, for example a hydrogel. An example of a collection assembly of the present invention is a mask layer, collection inserts, and a retaining layer where the layers are held in appropriate, functional relationship to each other but are not necessarily a laminate, i.e., the layers may not be bonded together. The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners. The layers of the assembly are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode.

"Substantially planar" as used herein, includes a planar surface that contacts a slightly curved surface, for example, a forearm or upper arm of a subject. A "substantially planar" surface is, for example, a surface having a shape to which skin can conform, i.e., contacting contact between the skin and the surface.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

The term "enzyme" intends any compound or material which catalyzes a reaction between molecules to produce one or more reaction products. The term thus includes protein enzymes, or enzymatically active portions (fragments) thereof, which proteins and/or protein fragments may be isolated from a natural source, or recombinantly or synthetically produced. The term also encompasses designed synthetic enzyme mimetics.

The term "time-dependent signal decline" refers to a detectable decrease in measured signal over time when no decrease or change in analyte concentration is actually occurring. The decrease in signal over time may be due to a number of different phenomena.

The term "signal-to-noise ratio" describes the relationship between the actual signal intended to be measured and the variation in signal in the absence of the analyte. The terms "S/N" and "SNR" are also used to refer to the signal-to-noise ratio. "Noise," as used herein, refers to any undesirable signal which is measured along with the intended signal.

General Methods

The present invention relates to use of a device for transdermally extracting and measuring the concentration of a target analyte present in a biological system. In preferred embodiments, the sensing device comprises a biosensor. In other preferred embodiments, a sampling device is used to extract small amounts of a target analyte from the biological system, and then sense and/or quantify the concentration of the target analyte. Measurement with the biosensor and/or sampling with the sampling device can be carried out in a continual or continuous manner. Continual or continuous measurements allow for closer monitoring of target analyte concentration fluctuations.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (in this case glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxide-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

The methods for measuring the concentration of a target analyte can be generalized as follows. An initial step (Step A) entails obtaining a raw signal from a sensing device, which signal is related to a target analyte present in the biological system. The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the signal including, but not limited to, physical, chemical, electrochemical, photochemical, spectrophotometric, polarimetric, colorimetric, radiometric, or like elements. In preferred embodiments of the invention, a biosensor is used which comprises an electrochemical sensing element.

After the raw signal has been obtained, the signal can undergo a data screening method (Step B) in order to eliminate outlier signals and/or poor (incorrect) signals using a predefined set of selection criteria. In addition, or alternatively, the raw signal can be converted in a conversion step (Step C) which can (i) remove or correct for background information, (ii) integrate the signal over a sensing time period, (iii) perform any process which converts the signal from one signal type to another, or (iv) perform any combination of steps (i), (ii) and/or (iii). In preferred embodiments, the conversion step entails a baseline background subtraction method to remove background from the raw signal and an integration step. In other embodiments, the conversion step can be tailored for use with a sensing device that provides both active and reference (blank) signals; wherein mathematical transformations are used to individually smooth active and reference signals, and/or to subtract a weighted reference (blank) signal from the active signal. In still further embodiments, the conversion step includes correction functions which account for changing conditions in the biological system and/or the biosensor system (e.g., temperature fluctuations in the biological system, temperature fluctuations in the sensor element, skin conductivity fluctuations, or combinations thereof). The result of the conversion step is an initial signal output which provides a value which can be correlated with the concentration of the target analyte in the biological sample.

In a calibration step (Step D), the raw signal obtained from Step A, or the initial signal obtained from Step B and/or Step C, is converted into an analyte-specific value of known units to provide an interpretation of the signal obtained from the sensing device. The interpretation uses a one-to-one mathematical transformation to model the relationship between a measured response in the sensing device and a corresponding analyte-specific value. Thus, the calibration step is used herein to relate, for example, an electrochemical signal (detected by a biosensor) with the concentration of a target analyte in a biological system. In one embodiment, the calibration step entails calibrating the sensing device using a single- or multi-point calibration, and then converting post-calibration data using correlation factors, time corrections and constants to obtain an analyte-specific value. Further signal processing can be used to refine the information obtained in the calibration step, for example, where a signal processing step is used to correct for signal differences due to variable conditions unique to the sensor element used to obtain the raw signal. In one embodiment, this further step is used to correct for signal time-dependence, particularly signal decline. In another embodiment, a constant offset term is obtained, which offset is added to the signal to account for a non-zero signal at an estimated zero analyte concentration.

The analyte value obtained using the above techniques can optionally be used in a subsequent step (Step E) to predict future (time forecasting) or past (calibration) measurements of the target analyte concentration in the biological system. For example, a series of analyte values are obtained by performing any combination of Steps A, B, C, and/or D in an iterative manner. This measurement series is then used to predict unmeasured analyte values at different points in time, future or past. In this manner, lag times inherent in certain sampling and/or sensing techniques can be reduced or eliminated to provide real time measurement predictions.

In another optional step, analyte values obtained using the above techniques can be used in a subsequent step (Step F) to control an aspect of the biological system. In one embodiment, the analyte value obtained in Step D is used to determine when, and at what level, a constituent should be added to the biological system in order to control an aspect of the biological system. In a preferred embodiment, the analyte value can be used in a feedback control loop to control a physiological effect in the biological system.

The above general methods (Steps A through F) are each independently useful in analyte sensing systems and can, of course, be used in a wide variety of combinations selected for a particular biological system, target analyte, and/or sensing technique. For example, in certain applications, a measurement sequence can include Steps A, C, D, E and F, in other applications, a measurement sequence can include Steps A, B, C and D, and the like. The determination of particularly suitable combinations is within the skill of the ordinarily skilled artisan when directed by the instant disclosure. Furthermore, Steps C through F are preferably embodied as one or more mathematical functions as described herein below. These functions can thus be carried out using a microprocessor in a monitoring system. Although these methods are broadly applicable to measuring any chemical analyte and/or substance in a biological system, the invention is expressly exemplified for use in a non-invasive, transdermal sampling system which uses an electrochemical biosensor to quantify or qualify glucose or a glucose metabolite.

Step A
Obtaining the Raw Signal

The raw signal can be obtained using any sensing device that is operatively contacted with the biological system. Such sensing devices can employ physical, chemical, electrochemical, spectrophotometric, polarimetric, colorimetric, radiometric, or like measurement techniques. In addition, the sensing device can be in direct or indirect contact with the biological system, or used with a sampling device which extracts samples from the biological system using invasive, minimally invasive or non-invasive sampling techniques. In preferred embodiments, a minimally invasive or non-invasive sampling device is used to obtain samples from the biological system, and the sensing device comprises a biosensor with an electrochemical sensing element. In particularly preferred embodiments, a sampling device is used to obtain continual transdermal or transmucosal samples from a biological system, and the analyte of interest is glucose.

More specifically, a non-invasive glucose monitoring device is used to measure changes in glucose levels in an animal subject over a wide range of glucose concentrations. The sampling method is based on transdermal glucose extraction and the sensing method is based on electrochemical detection technology. The device can be contacted with the biological system continuously, and automatically obtains glucose samples in order to measure glucose concentration at preprogrammed intervals.

Sampling is carried out continually by non-invasively extracting glucose through the skin of the patient. More particularly, an iontophoretic current is applied to a surface of the skin of a subject. When the current is applied, ions or charged molecules pull along other uncharged molecules or particles such as glucose which are drawn into a collection reservoir placed on the surface of the skin. The collection reservoir may comprise any ionically conductive material and is preferably in the form of a hydrogel which is comprised of a hydrophilic material, water and an electrolyte.

The collection reservoir may further contain an enzyme which catalyzes a reaction of glucose to form an easily detectable species. The enzyme is preferably glucose oxidase (GOx) which catalyzes the reaction between glucose and oxygen and results in the production of hydrogen peroxide. The hydrogen peroxide reacts at a catalytic surface of a biosensor electrode, resulting in the generation of electrons which create a detectable biosensor current (raw signal). Based on the amount of biosensor current created over a given period of time, a measurement is taken, which measurement is related to the amount of glucose drawn into the collection reservoir over a given period of time. In a preferred embodiment, the reaction is allowed to continue until substantially all of the glucose in the collection reservoir has been subjected to a reaction and is therefore no longer detectable, and the biosensor current generated is related to the concentration of glucose in the subject at the approximate time of sample collection.

When the reaction is complete, the process is repeated and a subsequent measurement is obtained. More specifically, the iontophoretic current is again applied, glucose is drawn through the skin surface into the collection reservoir, and the reaction is catalyzed in order to create a biosensor current. These sampling (extraction) and sensing operations are integrated such that glucose is extracted into the hydrogel collection pad where it contacts the GOx enzyme. The GOx enzyme converts glucose and oxygen in the hydrogel to hydrogen peroxide which diffuses to the sensor and is catalyzed by the sensor to regenerate oxygen and form electrons. The electrons generate an electrical signal that can be measured, analyzed, and correlated to blood glucose.

Optionally, one or more additional "active" collection reservoirs (each containing the GOx enzyme) can be used to obtain measurements. In one embodiment, two active collection reservoirs are used, and an average is taken between signals from the reservoirs for each measurement time point. Obtaining multiple signals, and then averaging reads from each signals, allows for signal smoothing of unusual data points from a sensor that otherwise may not have been detected by data screening techniques. Furthermore, skin site variability can be detected, and "lag" and/or "lead" differences in blood glucose changes relative to extracted glucose changes can be mitigated. In another embodiment, a second collection reservoir can be provided which does not contain the GOx enzyme. This second reservoir can serve as an internal reference (blank) for the sensing device, where a biosensor is used to measure the "blank" signal from the reference reservoir which signal is then used in a blank subtraction step as described below.

A generalized method for continual monitoring of a physiological analyte is disclosed in International Publication No. WO 97/24059, published Jul. 10, 1997, which publication is incorporated herein by reference. As noted in that publication, the analyte is extracted into a reservoir containing a hydrogel which is preferably comprised of a hydrophilic material of the type described in International Publication No. WO 97/02811, published Jan. 30, 1997, which publication is incorporated herein by reference. Suitable hydrogel materials include polyethylene oxide, polyacrylic acid, polyvinylalcohol and related hydrophilic polymeric materials combined with water to form an aqueous gel.

In the above non-invasive glucose monitoring device, a biosensor electrode is positioned on a surface of the hydrogel opposite the surface contacting the skin. The sensor electrode acts as a detector which detects current generated by hydrogen peroxide in the redox reaction, or more specifically detects current which is generated by the electrons generated by the redox reaction catalyzed by the platinum surface of the electrode. The details of such electrode assemblies and devices for iontophoretic extraction of glucose are disclosed in International Publication No. WO 96/00110, published Jan. 4, 1996, and International Publication No. WO 97/10499, published Mar. 2, 1997, which publications are also incorporated herein by reference.

Figure 1B:
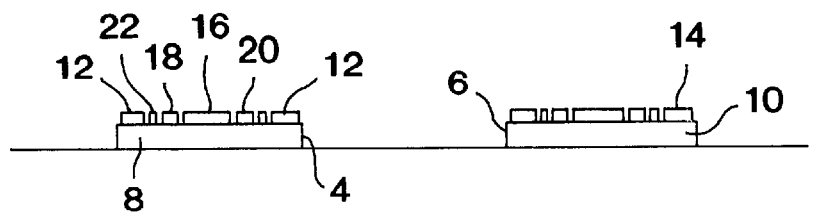
FIG. 1B depicts the side view of the iontophoretic collection reservoir and electrode assembly shown in FIG. 1A.

Referring now to FIGS. 1A and 1B, an iontophoretic collection reservoir and electrode assembly for use in a transdermal sensing device is generally indicated at 2. The assembly comprises two iontophoretic collection reservoirs, 4 and 6, each having a conductive medium 8, and 10 (preferably cylindrical hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described in detail below. A similar biosensor electrode arrangement can be contacted with the conductive medium 10, or the medium can not have a sensor means contacted therewith.

Figure 2:
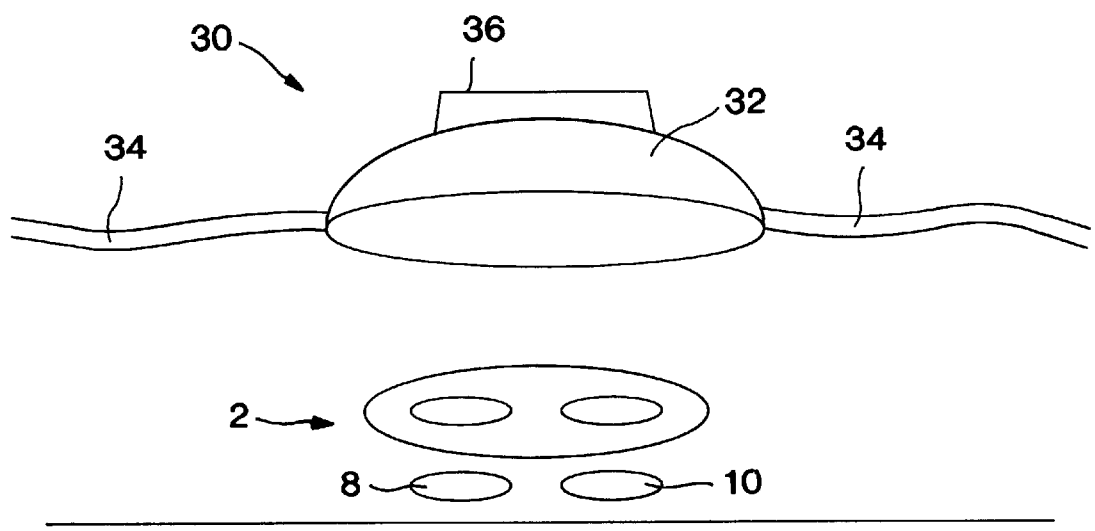
FIG. 2 is a pictorial representation of an iontophoretic sampling device which includes the iontophoretic collection reservoir and electrode assembly of FIGS. 1A and 1B.

Referring now to FIG. 2, an exploded view of the key components from a preferred embodiment of an iontophoretic sampling system is presented. In FIG. 2, the iontophoretic collection reservoir and electrode assembly 2 of FIGS. 1A and 1B is shown in exploded view in combination with a suitable iontophoretic sampling device housing 32. The housing can be a plastic case or other suitable structure which preferably is configured to be worn on a subjects arm in a manner similar to a wrist watch. As can be seen, conductive media 8 and 10 (hydrogel pads) are separable from the assembly 2; however, when the assembly 2 and the housing 32 are assembled to provide an operational iontophoretic sampling device 30, the media are in contact with the electrodes to provide a electrical contact therewith.

Figure 3:
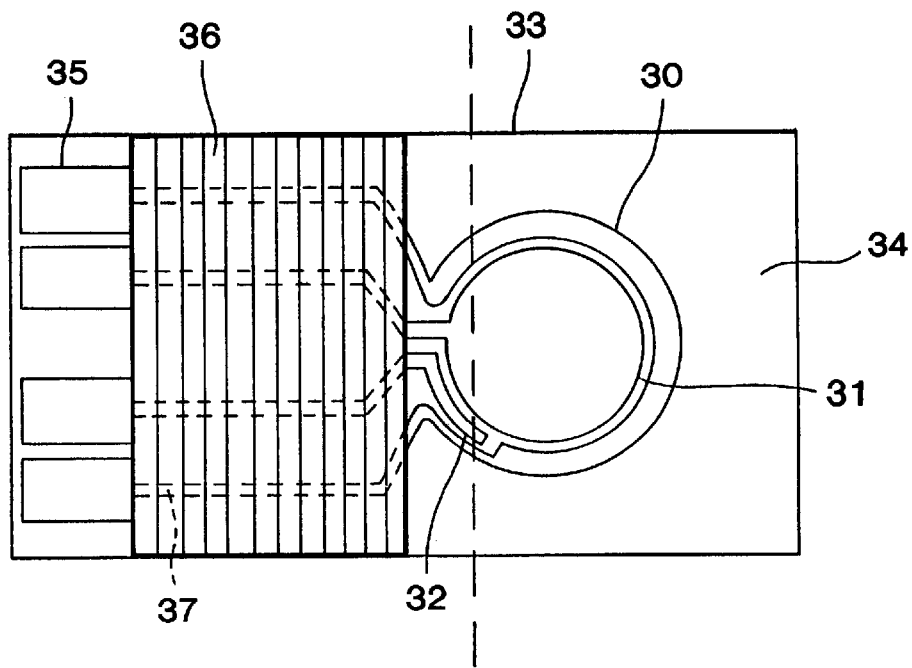
FIG. 3 is a representation of one embodiment of a bimodal electrode design. The figure presents an overhead and schematic view of the electrode assembly 33. In the figure, the bimodal electrode is shown at 30 and can be, for example, a Ag/AgCl iontophoretic/counter electrode. The sensing or working electrode (made from, for example, platinum) is shown at 31. The reference electrode is shown at 32 and can be, for example, a Ag/AgCl electrode. The components are mounted on a suitable nonconductive substrate 34, for example, plastic or ceramic. The conductive leads 37 leading to the connection pad 35 are covered by a second nonconductive piece 36 of similar or different material. In this example of such an electrode the working electrode area is approximately 1.35 cm$^2$. The dashed line in FIG. 3 represents the plane of the cross-sectional schematic view presented in FIG. 4.

In one embodiment, the electrode assemblies can include bimodal electrodes as shown in FIG. 3.

Figure 5:
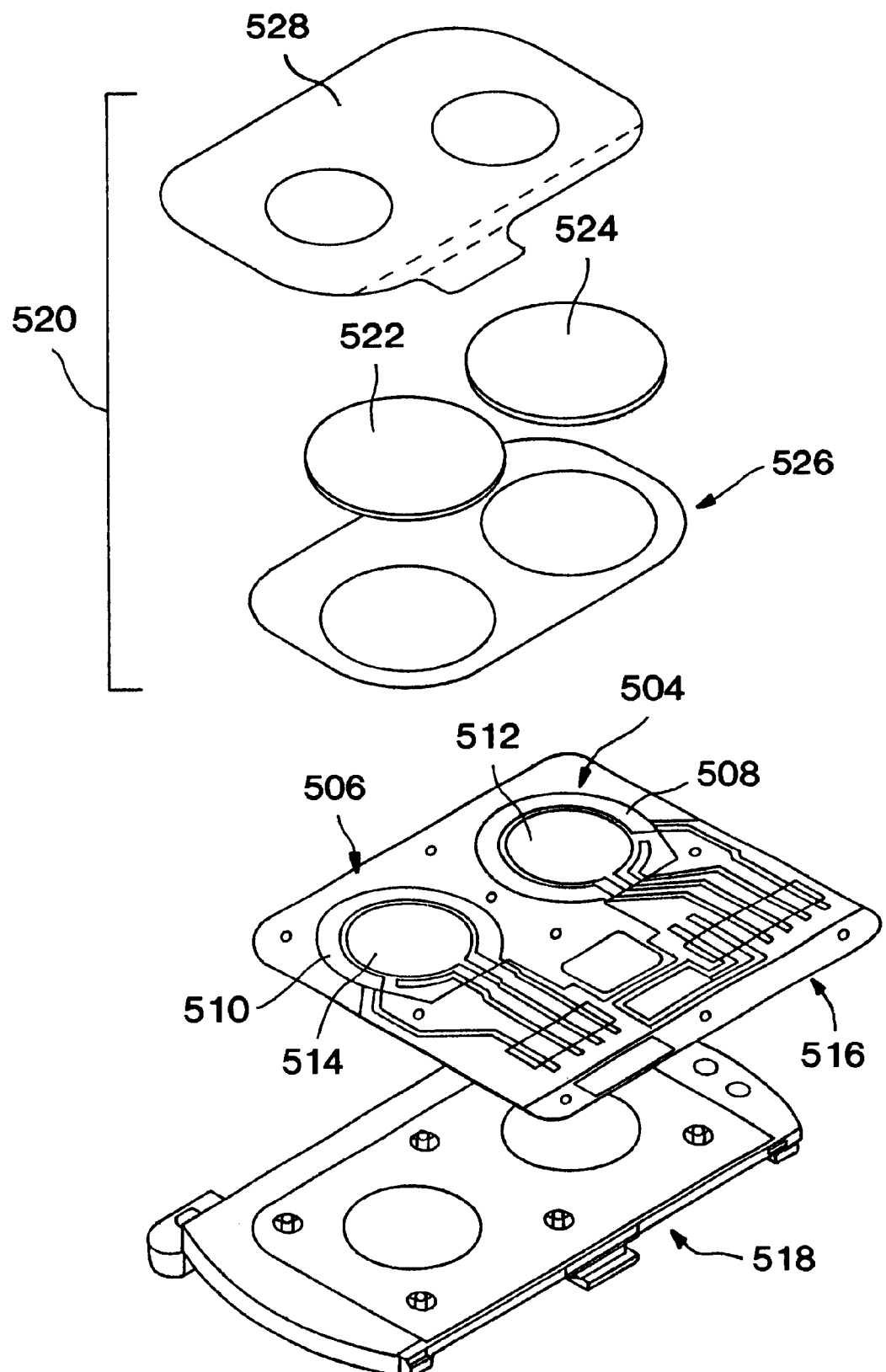
FIG. 5 is an exploded pictorial representation of components from a preferred embodiment of the automatic sampling system of the present invention.

Referring now to FIG. 5, an exploded view of the key components from one embodiment of an iontophoretic sampling system (e.g., one embodiment of an autosensor assembly) is presented. The sampling system components include two biosensor/iontophoretic electrode assemblies, 504 and 506, each of which have an annular iontophoretic electrode, respectively indicated at 508 and 510, which encircles a biosensor 512 and 514. The electrode assemblies 504 and 506 are printed onto a polymeric substrate 516 which is maintained within a sensor tray 518. A collection reservoir assembly 520 is arranged over the electrode assemblies, wherein the collection reservoir assembly comprises two hydrogel inserts 522 and 524 retained by a gel retaining layer 526 and a mask layer 528.

In one embodiment, the electrode assemblies can include bimodal electrodes as shown in FIG. 3. Modifications and additions to the embodiment of FIG. 5 will be apparent to those skilled in the art in light of the teachings of the present specification.

The components described herein are intended for use in a automatic sampling device which is configured to be worn like an ordinary wristwatch. As described in International Publication No. WO 96/00110, published Jan. 4, 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiment of FIG. 2 will be apparent to those skilled in the art in light of the teachings of the present specification.

A power source (e.g., one or more rechargeable or non-rechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 mA/cm$^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. The housing 32 can further include an optional temperature sensing element (e.g., a thermistor, thermometer, or thermocouple device) which monitors the temperature at the collection reservoirs to enable temperature correction of sensor signals as described in detail below. The housing can also include an optional conductance sensing element (e.g., an integrated pair of electrodes) which monitors conductance at the skin or mucosal surface to enable data screening correction or invalidation of sensor signals as also described in detail below.

After a suitable iontophoretic extraction period, one or both of the sensor electrode sets can be activated in order to detect extracted substances including the analyte of interest. Operation of the iontophoretic sampling device 30 is controlled by a controller 36 (e.g., a microprocessor), which interfaces with the iontophoretic electrodes, the sensor electrodes, the power supply, the optional temperature and/or conductance sensing elements, a display and other electronics. For example, the controller 36 can include a programmable a controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods. A sensor confidence loop can be provided for continually monitoring the sampling system to insure proper operations.

Figure 4:
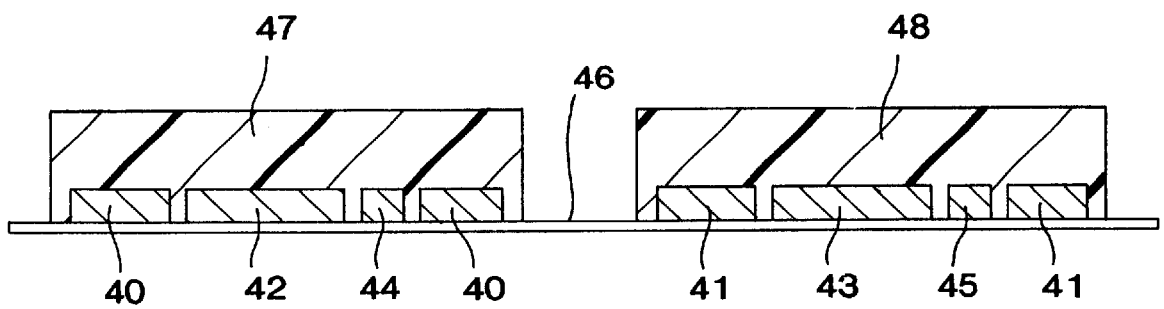
FIG. 4 is a representation of a cross-sectional schematic view of the bimodal electrodes as they may be used in conjunction with a reference electrode and a hydrogel pad. In the figure, the components are as follows: bimodal electrodes 40 and 41; sensing electrodes 42 and 43; reference electrodes 44 and 45; a substrate 46; and hydrogel pads 47 and 48.

In a further aspect, the sampling device can operate in an alternating polarity mode using first and second bimodal electrodes (FIGS. 4, 40 and 41) and two collection reservoirs (FIGS. 4, 47 and 48). Each bi-modal electrode (FIGS. 3, 30; FIGS. 4, 40 and 41) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIGS. 4, 44 and 45; FIGS. 3, 32) and sensing electrodes (FIGS. 4, 42 and 43; FIGS. 3, 31), as well as, the bimodal electrode (FIGS. 4, 40 and 41; FIGS. 3, 30) are connected to a standard potentiostat circuit during sensing. In general, practical limitations of the system require that the bimodal electrode will not act as both a counter and iontophoretic electrode simultaneously.

The general operation of an iontophoretic sampling system is the cyclical repetition of two phases: (1) a reverse-iontophoretic phase, followed by a (2) sensing phase. During the reverse iontophoretic phase, the first bimodal electrode (FIGS. 4, 40) acts as an iontophoretic cathode and the second bimodal electrode (FIGS. 4, 41) acts as an iontophoretic anode to complete the circuit. Analyte is collected in the reservoirs, for example, a hydrogel (FIGS. 4, 47 and 48). At the end of the reverse iontophoretic phase, the iontophoretic current is turned off. During the sensing phase, in the case of glucose, a potential is applied between the reference electrode (FIGS. 4, 44) and the sensing electrode (FIGS. 4, 42). The chemical signal reacts catalytically on the catalytic face of the first sensing electrode (FIGS. 4, 42) producing an electrical current, while the first bi-modal electrode (FIGS. 4, 40) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode should not limit the speed of the reaction at the sensing electrode. In the case of a large sensing electrode, the counter electrode should be able to source proportionately larger currents.

The design of the sampling system provides for a larger sensing electrode (see for example, FIG. 3) than previously designed. Consequently, the size of the bimodal electrode should be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Since the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100–400 mesh.

User control can be carried out using push buttons located on the housing 32, and an optional liquid crystal display (LCD) can provide visual prompts, readouts and visual alarm indications. The microprocessor generally uses a series of program sequences to control the operations of the sampling device, which program sequences can be stored in the microprocessor's read only memory (ROM). Embedded software (firmware) controls activation of measurement and display operations, calibration of analyte readings, setting and display of high and low analyte value alarms, display and setting of time and date functions, alarm time, and display of stored readings. Sensor signals obtained from the sensor electrodes are processed before storage and display by one or more signal processing functions or algorithms which are described in detail below. The microprocessor can also include an electronically erasable, programmable, read only memory (EEPROM) for storing calibration parameters (as described in detail below), user settings and all downloadable sequences.

Step B

Data Screening Methodologies

The raw signal obtained from the above-described glucose monitoring device can be screened to detect deviations from expected behavior which are indicative of poor or incorrect signals that will not correlate with blood glucose. Signals that are identified as poor or incorrect in this data screen may be discarded or otherwise corrected for prior to any signal processing and/or conversion in order to maintain data integrity. In the method of the invention, an objective set of selection criteria is established which can then be used to accept or discard signals from the sensing device. These selection criteria are device- and analyte-specific, and can be arrived at empirically by way of testing various devices in particular applications.

In the particular context of transdermal blood glucose monitoring using iontophoretic extraction and electrochemical detection, the following data screens can be employed. As discussed above, the iontophoretic extraction device can include two collection reservoirs. Thus, in active/blank systems, wherein one reservoir is active (contains the GOx enzyme) and one reservoir is blank, each reservoir contains an iontophoretic electrode and a sensing electrode. Signals from both the active and the blank reservoirs are screened, and an error in either the active, or the active and blank signal can be used to invalidate or correct the measurement from the cycle. In multiple active systems (wherein two or more reservoirs contain the GOx enzyme and iontophoretic and sensing electrodes), signals from one or more of the active reservoirs are screened, and an error in one can be used to invalidate or correct the measurement from the cycle.

As with any chemical sensing method, transient changes in temperature during or between measurement cycles, or between measurements of blank and active signals, can alter background signal, reaction constants and/or diffusion coefficients. Accordingly, a temperature sensor is used to monitor changes in temperature over time. A maximum temperature change over time (d(temp)/d(time)) threshold value can then be used in a data screen to invalidate a measurement. Such a threshold value can, of course, be set at any objective level, which in turn can be empirically determined depending upon the particular extraction/sensing device used, how the temperature measurement is obtained, and the analyte being detected. Absolute temperature threshold criteria can also be employed, wherein detection of high and/or low temperature extremes can be used in a data screen to invalidate a measurement. Temperature monitoring can be carried out using a separate, associated temperature sensing device, or, preferably using a temperature sensor that is integral with the sensing device. A large number of temperature sensing elements are known in the art (e.g., thermometers, thermistors, thermocouples, and the like) which can be used to monitor the temperature in the collection reservoirs.

Another data screen entails monitoring physiological conditions in the biological system, particularly monitoring for a perspiration threshold. In this regard, perspiration contains glucose, and perspiration occurring rapidly and in sufficient quantities may affect the detected signal either before or during biosensor measurement. Accordingly, a sensor can be used to monitor perspiration levels for a given measurement cycle at time points before, during, and/or after iontophoresis, and before, during, and/or after glucose sensing. Detection of perspiration levels that exceed an objective threshold is then used in a data screen to invalidate poor measurements. Although a number of different mechanisms can be used, skin conductance can be readily measured with a device contacted with the skin. Skin conductivity is related to perspiration. In one embodiment, if skin conductance as measured by a conductivity detector is greater than a predetermined level, then the corresponding measurement is invalidated.

Yet further data screens which are used in the practice of the invention take into consideration the expected behavior of the sampling/sensing device. In iontophoretic sampling, for example, there is a skin equilibration period before which measurements will generally be less accurate. During this equilibration period, the system voltage can be assessed and compared against an objective high voltage threshold. If this high voltage limit is exceeded, a data screen is used to exclude the corresponding analyte measurement, since the iontophoretic current was not at a target value due to high skin resistance (as indicted by the high voltage level).

In addition, the electrochemical signal during each sensing cycle is expected to behave as a smooth, monotonically decreasing signal which represents depletion of the hydrogen peroxide by the sensor electrode. Significant departure from this expected behavior is indicative of a poor or incorrect measurement (e.g., a non-monotonically decreasing signal is indicative of excessive noise in the biosensor signal), and thus monitoring signal behavior during sensing operations provides yet a further data screen for invalidating or correcting measurements.

Raw signal thresholds can also be used in the data screening method of the present invention. For example, any sensor reading that is less than some minimum threshold can indicate that the sampling/sensing device is not operating correctly, for example, where the biosensor electrode is disconnected. In addition, any chemical sensor will have a maximum range in which the device can operate reliably. A reading greater than some maximal value, then, indicates that the measurement is off-scale, and thus possibly invalid. Accordingly, minimum and maximum signal thresholds are used herein as data screens to invalidate or correct measurements. Such minimum and maximum thresholds can likewise be applied to background measurements.

A general class of screens can be applied that detect changes in signal, background, or voltage measurements. These screens are useful to assess the consistency of measurements and can detect problems or inconsistencies in the measurements. Error messages can be relayed to a display screen on the monitoring device, and/or, recorded to a log. Examples of such screens include the following:

(i) signal—Peak Stability. A large change in the peak of a sensor reading indicates a noisy signal. The peak of any given cathodal half cycle is defined as the difference between the first biosensor point and the temperature corrected average of the last two points from the previous anodal half cycle. If the percentage difference between successive peaks from the same sensor is greater than a predetermined value, for example, 30%, then an error is indicated.

(ii) background—Background Precision. Divergent readings at the end of biosensing indicate an unstable biosensor signal. Because these readings are used to assess background current for a particular cycle, an unstable signal may lead to an erroneous data point. If the difference between the last two anodal points (where the last two anodal points are typically the last two biosensor currents measured after anodal extraction) used to calculate the baseline is greater than or equal to a predetermined value, for example, 6 nA (or, e.g., a percentage of the first anodal point relative to the second anodal point), then an error is indicated.

(iii) background—Background Stability. This check is to determine if the background current is changing too excessively, which indicates a noisy signal and can result in inaccurate glucose readings. If the percentage difference between successive background measurements is greater than or equal to a predetermined value, for example, 15%, then an error is indicated.

(iv) voltage—Voltage Stability. If the glucose monitoring device is mechanically disturbed, there can be a larger change (e.g., larger relative to when the monitor is functioning under normal conditions) in iontophoresis voltage. This could lead to an aberrant reading. If the percentage difference between successive cathodal or anodal iontophoresis voltages is grater than a predetermined value, for example, 15%, then an error is indicated.

(v) voltage—Reference Electrode Check. When the electrode assembly includes a reference electrode (as when, for example, a bimodal electrode is employed) this check establishes the connectivity of the reference electrode to the sampling device and to the working electrode. The biosensor is activated such that a current should flow from the working electrode to the reference electrode. If the current measured is less than a threshold value, then an error is indicated and the measurement sequence can be terminated.

As will be appreciated by one of ordinary skill in the art upon reading this specification, a large number of other data screens can be employed without departing from the spirit of the present invention.

Step C
The Conversion Step

Continuing with the method of the invention, the above-described iontophoretic sampling device is used to extract the analyte from the biological system, and a raw amperometric signal (e.g., nanoampere (nA) signal) is generated from the associated electrochemical biosensor device. This raw signal can optionally be subjected to a data screening step (Step B) to eliminate poor or incorrect signals, or can be entered directly into a conversion step to obtain an initial signal output which is indicative of the amount of analyte extracted by the sampling system.

I. Ways of Obtaining Integrated Signals

1. Baseline Background

In one embodiment, the raw or screened raw signal is processed in the conversion step in order to remove or correct for background information present in the signal. For example, many sensor devices will have a signal whether or not an analyte of interest is present, i.e., the background signal. One such background signal is the "baseline background," which, in the context of electrochemical detection, is a current (nA) generated by the sensing device independent of the presence or absence of the analyte of interest. This baseline background interferes with measurement of analyte of interest, and the amount of baseline background can vary with time, temperature and other variable factors. In addition, electrochemically active interfering species and/or residual analyte can be present in the device which will further interfere with measurement of the analyte of interest.

This background can be transient background, which is a current generated independent of the presence or absence of the analyte of interest and which decreases over the time of sensor activation on the time scale of a measurement, eventually converging with the baseline background signal.

Accordingly, in one embodiment of the invention, a baseline background subtraction method is used during the conversion step in order to reduce or eliminate such background interferences from the measured initial signal output. The subtraction method entails activation of the electrochemical sensor for a sufficient period of time to substantially reduce or eliminate residual analyte and/or electrochemical signal that is not due to the analyte (glucose). After the device has been activated for a suitable period of time, and a stable signal is obtained, a measurement is taken from the sensor which measurement can then be used to establish a baseline background signal value. This background signal value is subtracted from an actual signal measurement value (which includes both analyte-specific and background components) to obtain a corrected measurement value. This baseline background subtraction method can be expressed using the following function:

$$i(\tau) = i_{raw}(\tau) - i_{bkgnd}(\tau)$$

wherein: ($i_{raw}(\tau)$) is the current measured by the sensor (in nA) at time $\tau$; ($\tau$) is the time after activation of the sensor; ($i_{bkgnd}(\tau)$) is the background current (in nA); and ($i(\tau)$) is the corrected current (in nA). Measurement of the baseline background signal value is taken close in time to the actual signal measurement in order to account for temperature fluctuations, background signal drift, and like variables in the baseline background subtraction procedure. The baseline background signal value can be integrated for use with coulometric signal processing, or used as a discrete signal value in amperometric signal processing. In particular embodiments of the invention, continual measurement by the iontophoretic sampling device provides a convenient source for the baseline background measurement, that is, after an initial measurement cycle has been completed, the baseline background measurement can be taken from a previous measurement (sensing) cycle.

2. Temperature Correcting Baseline Background

In yet another embodiment of the invention, the conversion step is used to correct for changing conditions in the biological system and/or the biosensor system (e.g., temperature fluctuations in the biological system, temperature fluctuations in the biosensor element, or combinations thereof). Temperature can affect the signal in a number of ways, such as by changing background, reaction constants, and/or diffusion coefficients. Accordingly, a number of optional temperature correction functions can be used in order to reduce these temperature-related effects on the signal.

In order to correct for the effect that temperature fluctuations or differences may have on the baseline background subtracted signal, the following temperature correction step can be carried out. More particularly, to compensate for temperature fluctuations, temperature measurements can be taken at each measurement time point within the measurement cycle, and this information can be used to base a temperature correction algorithm which adjusts the background current at every time point depending on the difference in temperature between that time point and the temperature when the previous background current was measured. This particular temperature correction algorithm is based on an Arrhenius relationship between the background current and temperature.

The temperature correction algorithm assumes an Arrhenius-type temperature dependence on the background current, such as:

$$i_{bkgnd} = A\exp\left[\frac{-K1}{T}\right]$$

wherein: ($i_{bkgnd}$) is the background current; (A) is a constant; (K1) is termed the "Arrhenius slope" and is an indication of how sensitive the current is to changes in temperature; and (T) is the temperature in °K.

Plotting the natural log of the background current versus the reciprocal of temperature provides a linear function having a slope of (-K1). Using a known or derived value of K1 allows the baseline current at any time (τ) to be corrected using the following function (which is referred to herein as the "K1 temperature correction"):

$$i_{bkgnd,corrected} = i_{bkgnd,\tau_0}\exp\left[-K1\left(\frac{1}{T_\tau} - \frac{1}{T_{\tau_0}}\right)\right]$$

wherein: ($i_{bkgnd,corrected}$) is the temperature corrected baseline current; ($i_{bkgnd,\tau0}$) is the baseline current at some reference temperature $T_{\tau0}$, for example, the baseline background measurement temperature; (K1) is the temperature correction constant; and ($T_\tau$) is the temperature at time τ. For the purposes of the invention, ($i_{bkgnd,\tau0}$) is usually defined as the "previous" baseline current. As can be seen, instead of making a time-independent estimation of the baseline current, the K1 temperature correction adjusts the baseline current in an Arrhenius fashion depending upon whether the temperature increases or decreases during or between biosensor cycles. Determination of the constant K1 can be obtained by plotting the natural log of the background current versus the reciprocal of the temperature for a learning set of data, and then using a best fit analysis to fit this plot with a line having a slope (-K1).

Raw or screened amperometric signals from Step A or Step B, respectively (whether or not subjected to the above-described baseline background subtraction and/or K1 temperature correction), can optionally be refined in the conversion step to provide integrated coulometric signals. In one particular embodiment of the invention, any of the above amperometric signals (e.g., the current generated by the sensor) can be converted to a coulometric signal (nanocoulombs (nC)), which represents the integration of the current generated by the sensor over time to obtain the charge that was produced by the electrochemical reaction.

In one embodiment, integration is carried out by operating the biosensor in a coulometric (charge-measuring) mode. Measuring the total amount of charge that passes through the biosensor electrode during a measurement period is equivalent to mathematically integrating the current over time. By operating in the coulometric mode, changes in diffusion constants resulting from temperature fluctuations, possible changes in the diffusion path length caused by uneven or non-uniform reservoir thickness, and changes in sensor sensitivity, have little effect on the integrated signal, whereas these parameters may have a greater effect on single point (current) measurements. Alternatively, a functionally equivalent coulometric measurement can be mathematically obtained in the method of the invention by taking discrete current measurements at selected, preferably small, time intervals, and then using any of a number of algorithms to approximate the integral of the time-current curve. For example, integrated signal can be obtained as follows:

$$Y = \int_{\tau_1}^{\tau_2} i(\tau)d\tau$$

wherein: (Y) is the integrated signal (in nC); and (i(τ)) is a current at time τ, and can be equal to $i_{raw}(\tau)$ for an uncorrected raw signal, or $i_{raw}(\tau)-i_{bkgnd}(\tau)$ for a baseline background subtracted signal, or $i_{raw}(\tau)-i_{bkgnd,corrected}(\tau)$ for a baseline background subtracted and temperature corrected signal.

3. Temperature Correction of Active Versus Blank Integrals

An additional temperature correction algorithm can be used herein to compensate for temperature dependence of a transient background (blank) signal. That is, in the active/blank sampling system exemplified hereinabove, the analyte measurement (blood glucose) is generated by integrating an active signal and subtracting therefrom a blank signal (see the blank subtraction method, infra). The blank integral may be "artifactually" high or low depending upon whether blank signal was measured at a higher or lower temperature than the active signal. In order to normalize the blank integral to the temperature at which the active signal was measured, the following function can be used (which is referred to herein as the "K2 temperature correction"):

$$Y_{blank,corrected} = Y_{blank}\exp\left[-K2\left(\frac{1}{T^n_{act}} - \frac{1}{T^n_{blank}}\right)\right]$$

wherein: ($Y_{blank,corrected}$) is the corrected blank integral; ($Y_{blank}$) is the uncorrected blank integral (in nC); (K2) is the "blank integral correction constant"; and ($T^n_{act}$) and ($T^n_{blank}$) are the average temperature of the active and blank signal, respectively. The average temperature is obtained from averaging the first n temperatures, such that (n) is also an adjustable parameter. Determination of the constant K2 can be obtained from an Arrhenius plot of the log of the blank integral against $1/T^n_{blank}$, using the reciprocal of the average of the first n temperature values, and then using a best fit analysis to fit this plot with a line having a slope (-K2).

Alternative temperature corrections which can be performed during the conversion step are as follows. In one embodiment, an integral average temperature correction is used wherein, for each measurement cycle, the integral average temperature is determined by the function:

$$\langle T \rangle = \frac{1}{T_f} \int_0^{T_f} T dt$$

and then correcting for the temperature at subsequent time points using the function:

$$Y_{t,corrected} = Y_t \exp\left[-a\left(\frac{\langle T_t \rangle - \langle T_{ref} \rangle}{\langle T_{ref} \rangle}\right)\right]$$

wherein: ($Y_t$) is the uncorrected signal at time t; ($Y_{t,corrected}$) is the corrected signal at time t; ($\langle T_t \rangle$) is the integral average temperature at time t; ($\langle T_{ref} \rangle$) is the integral average temperature at the reference time (e.g., the calibration time); (t) is the time after sensor measurement is first initiated; and (a) is an adjustable parameter which is fit to the data.

In other embodiments, temperature correction functions can be used to correct for temperature differences between multiple active signals, or between active and blank signals. For example, in the active/blank sensing device exemplified herein, blank subtraction is used to cancel out much of the temperature-dependence in the active signal. However, temperature transients during the monitoring period will result in varying background currents, which can result in signal errors when the current is multiplied by the total integration time in the instant conversion step. This is particularly true where the active and blank integrals are disjointed in time, and thus possibly comprised of sets of background current values that occurred at different temperatures.

4. Anodal Subtraction

In yet another alternative temperature correction, temperature measurements taken in the active and blank reservoirs at alternating anodal and cathodal phases during a measurement cycle are used in a subtraction method in order to reduce the impact of temperature fluctuations on the signals. In this regard, the active/blank reservoir iontophoretic sampling system can be run under conditions which alternate the active and blank reservoirs between anodal and cathodal phases during a measurement cycle. This allows the blank anodal signal to be measured at the same time as the active cathode signal, and temperature variations will likely have similar impact on the two signals. The temperature correction function thus subtracts an adjusted anodal signal (taken at the same time as the cathodal signal) from the cathodal signal in order to account for the effect of temperature on the background. More particularly, a number of related temperature correction functions which involve fractional subtraction of blank anode signals can be summarized as follows:

$$Y = Y_{act,cath} - d * Y_{blank,an}$$

$$Y = Y_{act,cath} - d * [Y_{blank,an} - (Y_{act,an} - Y_{blank,cath})]$$

$$Y = Y_{act,cath} - d * [Y_{blank,an} - (Y_{act,an} - Y_{blank,cath})]|_{ave\ t_1, t_2}$$

$$Y = Y_{act,cath} - d * [Y_{blank,an} - (Y_{blank,an} - Y_{blank,cath})]|_{ave\ t_1 - t_2}$$

$$Y = Y_{act,cath} - d * (Y_{blank,an} - AOS) * \left[\frac{Y_{blank,cath}}{Y_{act,an} - AOS}\right]\Bigg|_{ave\ t_1, t_2}$$

$$Y = Y_{act,cath} - d * (Y_{blank,an} - AOS) * \left[\frac{Y_{blank,cath}}{Y_{act,an} - AOS}\right]\Bigg|_{ave\ t_1 - t_2}$$

wherein: ($Y_{act,\ cath}$) is the active signal in the cathodal phase (in nC); ($Y_{blank,\ an}$) is the blank signal in the anodal phase (in nC); ($Y_{act,\ an}$) is the active signal in the anodal phase (in nC); ($Y_{blank,\ cath}$) is the blank signal in the cathodal phase (in nC); (Y) is the "blank anode subtracted" signal; (ave $t_1, t_2$) is the average of signals taken at two time points $t_1$ and $t_2$; (ave $t_1-t_2$) is the average of signals taken over the time period of $t_1-t_2$; (d) is a universal fractional weight and is generally a function of time; and (AOS) is a universal anodal offset which can be empirically obtained using standard mathematical techniques, and optionally adjusted using data taken from two previous time points, $t_1$ and $t_2$ (i.e., ave $t_1$, $t_2$) or using the average of data taken over the time period of $t_1-t_2$ (i.e., ave $t_1-t_2$).

In still further embodiments of the invention, the conversion step can include a blank subtraction step, combined data from two active reservoirs, and/or a smoothing step.

The blank subtraction step is used to subtract the blank signal from the active signal in order to remove signal components that are not related to the analyte, thus obtaining a cleaner analyte signal. When raw signal is obtained from two active reservoirs the two raw signals can be averaged or a summed value of the two raw signals can be used. In the smoothing step, mathematical transformations are carried out which individually smooth signals obtained from the active and blank collection reservoirs. These smoothing algorithms help improve the signal-to-noise ratio in the biosensor, by allowing one to correct the signal measurements obtained from the device to reduce unwanted noise while maintaining the actual signal sought.

More particularly, a blank subtraction step is used in the active-blank iontophoretic sampling system of the invention as follows. Signals from the blank (second) reservoir, taken at, or about the same time as signals from the active (first) reservoir, are used to substantially eliminate signal components from the active signal that are not specifically related to the analyte. In this regard, the blank reservoir contains all of the same components as the active reservoir except for the GOx enzyme, and the blank signal should thus exhibit similar electrochemical current to the active signal, except for the signal associated with the analyte. Accordingly, the following function can be used to subtract the blank signal from the active signal:

$$Y_t = Y_{t,act} - d * Y_{t,blank}$$

wherein: ($Y_{t,act}$) is the active signal (in nC) at time t; ($Y_{t,blank}$) is the blank signal (in nC) at time t; ($Y_t$) is the "blank subtracted" signal at time t; and (d) is the time-dependent fractional weight for the blank signal, and d preferably=1. In relation to the equation shown above that is used to subtract the blank signal from the active signal, when two active reservoirs are used d preferably=−1, or, more generally, as shown in the equation below, the summed signal can be "weighted" to account for different contributions of signal from each reservoir.

In the case of two active reservoirs, each reservoir is capable of generating raw signal and each contains all of the same components. For example, where two collection reservoirs are used for detecting glucose both reservoirs contain glucose oxidase. Accordingly, the following function can be used:

$$Y_{t,c} = aY_{t,act1} + bY_{t,act2}$$

wherein: "a" is the time-dependent fractional weight for the first active signal; ($Y_{t,act1}$) is the first active signal (in nC) at time t; "b" is the time-dependent fractional weight for the second active signal; ($Y_{t,act2}$) is the second active signal (in nC) at time t; ($Y_{t,c}$) is the summed signal at time t.

II. General Procedures for Smoothing Integrated Signals

In the smoothing step, the active signal obtained from the first (active) reservoir can be smoothed using a smoothing function. In multiple active systems, the same smoothing can be applied to each signal before summing. In one embodiment, the function can be expressed as a recursive function as follows:

$$E_{t,act} = w_{act} Y_{t,act} + (1-w_{act})(E_{t-1,act})$$

wherein: $(Y_{t,act})$ is the measurement of the active signal (in nC) at time t; $(E_{t,act})$ is the estimate of the active signal (in nC) at time t for t>1 (at t=1, $E_{t,act}=Y_{t,act}$); and $(w_{act})$ is the "estimate weight" for the active biosensor, wherein $0 \leq w_{act} \leq 1$.

The reference (blank) signal obtained from the second reservoir can also be smoothed using a similar recursive smoothing function. This function can be expressed as follows:

$$E_{t,blank} = w_{blank} Y_{t,blank} + (1-w_{blank})(E_{t-1,blank})$$

wherein: $(Y_{t,blank})$ is the measurement of the blank signal (in nC) at time t; $(E_{t,blank})$ is the estimate of the blank signal (in nC) at time t for t>1 (at t=1, $E_{t,blank}=Y_{t,blank}$); and $(w_{blank})$ is the "estimate weight" for the blank biosensor, wherein $0 \leq w_{blank} \leq 1$.

Once the active and blank signals have been individually smoothed, the blank signal can be subtracted from the active signal in order to obtain a signal that is indicative of the glucose reaction only. As discussed above, the blank signal should exhibit a similar electrochemical current to the active signal, except for the signal associated with the glucose analyte. In the practice of the invention, this blank subtraction step can subtract the value of the smoothed blank signal per se, or a weighted blank signal can be subtracted from the active signal, using the following function to obtain a fractional subtraction:

$$E_t = E_{t,act} - d^* E_{t,blank}$$

wherein: $(E_{t,act})$ is the estimate of the active signal (in nC) at time t; $(E_{t,blank})$ is the estimate of the blank signal (in nC) at time t; $(E_t)$ is the "blank subtracted" smoothed sensor signal at time t; and (d) is the time-dependent fractional weight for the blank signal.

The same recursive function can be used wherein the order of the smoothing and blank subtraction steps are reversed such that: $(Y_{t,act})$ is the integral of the active signal (in nC) at time t; $(Y_{t,blank})$ is the integral of the blank signal (in nC) at time t; $(Y_t)$ is the "blank subtracted" sensor signal (in nC) at time t; (d) is the time-dependent fractional weight for the blank signal; and $$Y_t = Y_{t,act} - d^* Y_{t,blank}$$

$$E_t = wY_t + (1-w)(E_{t-1})$$

This smoothing can alternatively be carried out on discrete (nA) sensor signals, with or without temperature and/or background subtraction corrections. Smoothing can also be carried out on active signals or on averages of two or more active signals. Further modifications to these functions will occur to those of ordinary skill in the art, in light of the present enabling disclosure.

Step D
The Calibration Step

Continuing with the method of the invention, any of the raw signals obtained from Step A, the screened raw signal obtained from Step B, or the initial output signal obtained from Step C (or from Steps B and C), can be converted into an analyte-specific value using a calibration step which correlates the signal obtained from the sensing device with the concentration of the analyte present in the biological system. A wide variety of calibration techniques can be used to interpret such signals. These calibration techniques apply mathematical, statistical and/or pattern recognition techniques to the problem of signal processing in chemical analyses, for example, using neural networks, genetic algorithm signal processing, linear regression, multiple-linear regression, partial linear regression, deconvolution, or principal components analysis of statistical (test) measurements.

One method of calibration involves estimation techniques. To calibrate an instrument using estimation techniques, it is necessary to have a set of exemplary measurements with known concentrations referred to as the calibration set (e.g., reference set). This set consists of m samples, each with n instrument variables contained in an m by n matrix (X), and an m by 1 vector (y), containing the concentrations. If a priori information indicates the relationship between the measurement and concentration is linear, the calibration will attempt to determine an n by 1 transformation or mapping (b), such that $$y=Xb$$

is an optimal estimate of y according to a predefined criteria. Numerous suitable estimation techniques useful in the practice of the invention are known in the art. These techniques can be used to provide constant parameters, which can then be used in a mathematical transformation to obtain a measurement value indicative of the concentration of analyte present in the biological system at the times of measurement.

In one particular embodiment, the calibration step may be carried out using artificial neural networks or genetic algorithms. The structure of a particular neural network algorithm used in the practice of the invention can vary widely; however, the network should contain an input layer, one or more hidden layers, and one output layer. Such networks can be optimized on training data set, and then applied to a population. There are an infinite number of suitable network types, transfer functions, training criteria, testing and application methods, which will occur to the ordinarily skilled artisan upon reading the instant specification.

In the context of the iontophoretic glucose sampling device described hereinabove (which can contain an active collection reservoir—with the GOx enzyme, and a blank collection reservoir; or alternately, two active reservoirs with the GOx enzyme), a preferred neural network algorithm would use, for example, inputs selected from the following to provide a blood glucose measurement: elapsed time since calibration; signal from the active reservoir; signal from the blank reservoir; signal from two active reservoirs (either averaged or summed); calibration time; measured temperature; applied iontophoretic voltage; skin conductance; blood glucose concentration, determined by an independent means, at a defined calibration point; background; background referenced to calibration; and, when operating in the training mode, measured glucose.

Whether or not the calibration step is carried out using conventional statistical techniques or neural network algorithms, the calibration step can include a universal calibration process, a single-point calibration process, or a multi-point calibration process. In one embodiment of the invention, a universal calibration process is used, wherein the above mathematical techniques are used to derive a correlation factor (or correlation algorithm) that allows for accurate, dependable quantification of analyte concentration by accounting for varying backgrounds and signal interferences irrespective of the particular biological system being monitored. In this regard, the universal calibrant is selected to provide a close correlation (i.e., quantitative association) between a particular instrument response and a particular analyte concentration, wherein the two variables are correlated.

In another embodiment, a single-point calibration is used. More particularly, the single-point calibration process can be used to calibrate measurements obtained by iontophoretic sampling methodologies using a reference measurement obtained by conventional (invasive) methods. Single-point calibration allows one to account for variables that are unique to the particular biological system being monitored, and the particular sensing device that is being used. In this regard, the transdermal sampling device is generally contacted with the biological system (placed on the surface of a subject's skin) upon waking. After the device is put in place, it is preferable to wait a period of time in order allow the device to begin normal operations.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

In the context of glucose monitoring, a blood sample can be extracted when the device has attained normal operations, such that the invasive blood sample extraction is taken in a corresponding time period with a measurement cycle. Actual blood glucose levels can then be determined using any conventional method (e.g., colorimetric, electrochemical, spectrophotometric, or the like) to analyze the extracted sample. This actual value is then used as a reference value in the single-point calibration process, wherein the actual value is compared against the corresponding measured value obtained with the transdermal sampling device. In yet another embodiment, a multi-point calibration process is used, wherein the above-described single-point calibration process is repeated at least once to provide a plurality of point calibrations. For example, the multi-point calibration process can be carried out at various time intervals over the course of a continual or continuous measuring period.

Continuing with the calibration step, the signals obtained from Step B and/or Step C, supra, can be subjected to further signal processing prior to calibration as follows. Referring particularly to the baseline background subtraction method of the conversion step (Step C), the corrected signal should theoretically be directly proportional to the amount of analyte (glucose) present in the iontophoretically extracted sample. However, sometimes a non-zero intercept is obtained in the correlation between signal and reference glucose value. Accordingly, a constant offset term (which can be positive or negative) is obtained which can be added to the converted signal to account for a non-zero signal at an estimated zero blood glucose concentration. The offset can be added to the active sensor signal; or, in the case of an iontophoretic sampling system that obtains both active and blank signals, the offset can be added to the blank-subtracted active signal.

The calibration step can be carried out using, for example, the single-point calibration method described hereinabove. The reference blood glucose concentration thus obtained can then be used in the following conversion factor:

$$b_{gain} = \frac{BG_{cal} + \rho}{E_{cal} + OS}$$

wherein: ($E_{cal}$) is the blank-subtracted smoothed sensor signal (in nC) at calibration; ($BG_{cal}$) is the reference blood glucose concentration (in mg/dL) at calibration; ($b_{gain}$) is the conversion factor [(mg/dL) /nC]; (OS) is the offset calibration factor constant (in nC) which can be calculated using standard regression analysis; and ($\rho$) is the calibration offset (in mg/dL). Post calibration data can then be converted using the following function:

$$EG_t = b_{gain}[E_t + OS] - \rho$$

wherein ($EG_t$) is the estimated blood glucose concentration (in mg/dL). Other signal values, such as $Y_t$, can be substituted for $E_t$ and $E_{cal}$ depending upon the amount of prior signal processing performed (see, e.g., Step C, supra).

Further signal processing can also be used to correct for time-dependent behavior related to the particular sensor element that is used in the sensing operation. In this regard, signal measurements of certain types (such as the electrochemical signal measurements described herein) exhibit change over time for reasons which are not fully understood. The present invention is not premised on any particular theory with respect to why such time-dependent change occurs. Rather, the invention recognizes that time-dependent behavior can occur, and corrects for this behavior using one or more mathematical functions.

Thus, in one embodiment, a corrected measurement can be calculated using a mathematical function which compensates for time-dependent decline in the biosensor signal between measurements during the period of continual or continuous measuring of the analyte concentration. The correction function uses one or more additive decay parameters ($\alpha_i$) and one or more multiplicative decay parameters ($\epsilon_i$), (both of which are empirically determined for the biosensor), and can be expressed as follows:

$$EG_t = b_{gain}[E_t(1+\epsilon_i t) + OS] + \alpha_i t - \rho$$

wherein:

$$b_{gain} = \frac{BG_{cal} + \rho - \alpha_i t_{cal}}{E_{cal}(1 + \epsilon_i t_{cal}) + OS}$$

and ($t_{cal}$) is the calibration point; ($EG_t$) is the estimated blood glucose concentration at time t; ($E_t$) is the analyte signal at time t; (OS) is the constant offset term which accounts for a non-zero signal at an estimated zero blood glucose concentration (as described above); ($\epsilon$) is a gain term for time-dependent signal decline and can have multiple time segments (e.g., i=1, 2, or 3); ($\alpha$) is a correction term for a linear time-dependent signal decline in the time segments and can have multiple time segments (e.g., i=1, 2, or 3); (t) is the elapsed time, and ($\rho$) is the calibration offset (in mg/dl).

In an alternative embodiment, a corrected measurement can be calculated using a mathematical function which compensates for time-dependent decline in the biosensor signal between measurements, during the period of continual or continuous measuring of the analyte concentration, by correlating signal at the beginning of the measurement series to a unit of decay. The correction function uses an additive decay parameter ($\alpha$) and a decay correction factor (γ). This equation allows a time-dependent multiplicative correction to be applied to the integrated signal in a manner that amplifies, to a greater extent, those signals that have been observed to decay at a greater rate (e.g., empirically, signals that give lower BGain tend to decay faster). Use of the BGAIN factor, as described herein, can insure that a reasonable calibration factor is obtained.

In this embodiment, $EG_t$, the calculated value of blood glucose at the measurement time, is computed as follows:

$$EG_t = \left(\left[\frac{BG_{cal} - \alpha t_{cal}}{E_{cal} + OS} - \gamma t_{cal}\right] + \gamma t\right) * (E_t + OS) + \alpha t$$

$$\text{where } BGAIN = \left[\frac{BG_{cal} - \alpha t_{cal}}{E_{cal} + OS} - \gamma t_{cal}\right]$$

wherein: $BG_{cal}$ is the true blood glucose at the calibration point; $E_{cal}$ is the analyte signal at calibration; ($t_{cal}$) is the elapsed time of the calibration point; ($EG_t$) is the estimated blood glucose concentration at time t; ($E_t$) is the analyte signal at time t; (OS) is the constant offset term which accounts for a non-zero signal at an estimated zero blood glucose concentration (as described above); (γ) is a time-dependent correction term for signal decline; (α) is a time-dependent correction term for signal decline; and (t) is the elapsed time.

Employing these equations a "time segmentation" can be performed as follows:

$$BGAIN_1 = \left[\frac{BG_{cal} - \alpha_1 t_{cal}}{E_{cal} + OS} - \gamma_1 t_{cal}\right] \text{ if } t < t_{12}$$

$$BGAIN_2 = \left[\frac{BG_{cal} - \alpha_1 t_{12} - \alpha_2(t_{cal} - t_{12})}{E_{cal} + OS} - \gamma_1 t_{12} - \gamma_2(t_{cal} - t_{12})\right]$$

$$\text{if } t_{12} < t_{cal} < t_{23}$$

$$BGAIN_3 = \left[\frac{BG_{cal} - \alpha_1 t_{12} - \alpha_2(t_{cal} - t_{12}) - \alpha_3(t_{cal} - t_{23})}{E_{cal} + OS} - \right.$$

$$\left. \gamma_1 t_{12} - \gamma_2(t_{cal} - t_{12}) - \gamma_3(t_{cal} - t_{23})\right]$$

if $t_{23} < t_{cal}$ $EG_t = (BGAIN_1 + \gamma_1 t) * (E_t + OS) + \alpha_1 t$ if $t < t_{12}$ $EG_t = (BGAIN_2 + \gamma_1 t_{12} + \gamma_2(t - t_{12})) * (E_t + OS) + \alpha_1 t_{12} + \alpha_2(t - t_{12})$ if $t_{12} < t < t_{23}$ $EG_t = (BGAIN_3 + \gamma_1 t_{12} + \gamma_2(t_{23} - t_{12}) + \gamma_3(t - t_{23})) * (E_t + OS) + \alpha_1 t_{12} + \alpha_2(t_{23} - t_{12}) + \alpha_3(t - t_{23})$ if $t_{23} < t$ wherein: $EG_t$ is the calculated value of blood glucose at the measurement time; $BG_{cal}$ is the true blood glucose at the calibration point, t is the elapsed time (hence $t_{cal}$ is the elapsed time at the calibration point), OS is the offset parameter, $\alpha_i$ and $\gamma_i$ are the time dependent correction terms to account for the declining signal with time. To avoid a dominant time correction term as the elapsed time increases, the time correction parameters $\alpha_i$ and $\gamma_i$ are distinct for three different time intervals ("i"): 0 to 6 hours (e.g., i=1), 6 to 10 hours (e.g., i=2), and 10 to 14 hours (e.g., i=3), as shown above. Therefore, $t_{12}$=6 hours and $t_{23}$=10 hours.

The time segmentation allows for greater flexibility in predicting non-linear signal decay terms.

The signal processing methods and techniques described in Steps A through D can be combined in a variety of ways to provide for improved signal processing during analyte measurement. In one embodiment, an active/blank sampling system is used to obtain the raw signal in Step A. These raw signals are then screened in Step B to obtain screened data. These screened data are then subjected to a temperature correction using the K1 temperature correction, and then converted using the baseline subtraction and integration methods of Step C. The converted data are also smoothed (both active and blank) using the smoothing functions of Step C, the smoothed data are temperature corrected using the K2 temperature correction, and a blank subtraction is carried out. The smoothed and corrected data are then converted to the analyte concentration in the biological system using the calibration methods of Step D to perform a single-point calibration, wherein the data is also refined using the offset and time-dependent behavior corrections to obtain a highly accurate analyte concentration value.

In another embodiment, if two active reservoirs ($A_1/A_2$) are used, a "sensor consistency check" can be employed that detects whether the signals from the reservoirs are changing in concert with one another. This check compares the percentage change from the calibration signal for each reservoir, then calculates the difference in percentage change in signal between the two reservoirs. If this difference is greater than some threshold, then the signals are not "tracking" one another and this data point can be screened as in Step B. This check verifies consistency between the two sensors. A large difference can indicate noise in the signals.

In yet another embodiment of the present invention a "Calibration Factor Check" may be employed. This check provides control over unreasonable finger prick measurements or incorrect entries and provides additional assurance that a reasonable calibration slope has been generated. Typically, there are two calibration factors that are calculated at calibration: BGAIN and CAL RATIO. If BGAIN is less than or equal to a predetermined threshold value, or if the CAL RATIO is greater than or equal to a predetermined threshold value, then a calibration error is indicated. Such an error can be displayed to the user, for example, a calibration window can appear on the monitor's display appear. Such an error indicates to the users that the user must perform the calibration again. For the Calibration Factor Check, CAL RATIO can be calculated as follows:

$$CALRATIO = \left[\frac{BG_{cal}}{E_{cal} + OS}\right]$$

wherein, $BG_{cal}$ is the true blood glucose at the calibration point; $E_{cal}$ is the analyte signal at calibration; and (OS) is the constant offset term which accounts for a non-zero signal at an estimated zero blood glucose concentration.

Step E

Time Forecasting Measurements

The corrected analyte value obtained using the above techniques can be used to predict future (e.g., time forecasting) or past (e.g., calibration) target analyte concentrations in the biological system. In one embodiment, a series of analyte values are obtained by performing any combination of Steps A, B, C, and/or D, supra, in an iterative manner. These measurements are then used to predict unmeasured analyte values at different points in time, future or past.

More particularly, the above-described iontophoretic sampling process is carried out in order to obtain three or more measurements of the target analyte. Using these measurements, an additional measurement can be calculated. The additional measurement is preferably calculated using a series function.

In the context of blood glucose monitoring, it has been found that the actual (real-time) glucose level in a subject differs from the measured glucose level obtained using a sampling device that extracts glucose from the subject using iontophoresis. The difference is due, in part, to a lag time between extracting the glucose analyte and obtaining a measurement from the extracted glucose. This lag time can vary depending on factors such as the particular subject using the device, the particular area of skin from which glucose is extracted, the type of collection reservoir used, and the amount of current applied. In order to compensate for this inherent lag time, the method of the present invention can utilize data obtained from previous measurements and a mathematical function in order to predict what a future analyte concentration will be. In this case, the predicted future reading can be used as a "real-time value" of the analyte level.

In another embodiment, mathematical methods can be used to predict past measurements, such as in the context of making a calibration. More particularly, measurements obtained using the above-described transdermal sampling device can be calibrated against one or more reference measurements obtained by conventional (blood extraction) methods. In such calibration processes, actual blood glucose levels are determined using conventional analytical methods (e.g., colorimetric, electrochemical, spectrophotometric, or the like) to analyze an extracted blood sample. These actual measurements are then compared with corresponding measurements obtained with the transdermal sampling device, and a conversion factor is then determined. In normal operations, the transdermal sampling device is generally first contacted with the biological system (placed on the surface of a subject's skin) upon waking. After the device is put in place, it is preferable to wait a period of time in order allow the device to attain normal operating parameters, after which time the device can be calibrated. However, if a blood sample is extracted at the time when the device is first applied (as would normally be most convenient), there may not be a corresponding signal from the transdermal sampling system which can be compared with the reference value obtained from the extracted blood sample. This problem can be overcome using prediction methods which allow one to perform a conventional blood glucose test (via a blood sample extraction) when the device is first applied, and then calibrate the device at a later time against the results of the conventional glucose test.

A number of mathematical methods for predicting future or past measurements can be used in the practice of the invention. For example, linear or nonlinear regression analyses, time series analyses, or neural networks can be used to predict such measurements. However, it is preferred that a novel combination of exponential smoothing and a Taylor series analysis be used herein to predict the future or past measurement.

A number of other physiological variables may be predicted using the above techniques. For example, these prediction methods can be used to time forecast those physiological variables that cannot be measured in real-time, or that demonstrate frequent fluctuations in their data. Examples of physiological functions and the variables that characterize them include, but are not limited to, cerebral blood flow (in the treatment of stroke patients) which is related to blood viscosity and the concentrations of plasma proteins and clotting factors in the blood stream (Hachinski, V. and Norris, J. W., "The Acute Stroke," Philadelphia, F. A. Davis, 1985); pulmonary function (in asthma patients) as measured by lung volumes in the different phases of respiration (Thurlbeck, W. M. (1990) *Clin. Chest Med.* 11:389); and heart activity (in recurrent cardiac arrest) as measured by electrical activity of the heart (Marriott, H. J. L., "Practical Electrocardiography", 8th Ed., Baltimore, Williams & Wilkins, 1983). Other examples of physiological variables that can be predicted, include renal dialysis, where blood concentrations of urea and blood gases are followed (Warnock, D. G. (1988) *Kidney Int.* 34:278); and anesthesia treatment, where various parameters (e.g., heart rate, blood pressure, blood concentration of the anesthesia) are monitored to determine when the anesthesia will stop functioning (Vender, J. S., and Gilbert, H. C., "Monitoring the Anesthetized Patient," in Clinical Anesthesia, 3rd Ed., by Barash et al., Lippincott-Raven Publishers, Philadelphia, 1996).

Step F
Controlling a Physiological Effect

The analyte value obtained using the above techniques can also be used to control an aspect of the biological system. e.g., a physiological effect. In one embodiment, an analyte value obtained as described above is used to determine when, and at what level, a constituent should be added to the biological system in order to control the concentration of the target analyte.

More particularly, in the context of blood glucose monitoring, use of prediction techniques (Step E, supra) allows for accurate predictions of either real-time or future blood glucose values. This is of particular value in predicting hypoglycemic episodes which can lead to diabetic shock, or even coma. Having a series of measurements obtained from the continual iontophoretic sampling device, and the capability to predict future values, allows a subject to detect blood glucose swings or trends indicative of hypoglycemic or hyperglycemic episodes prior to their reaching a critical level, and to compensate therefor by way of exercise, diet or insulin administration.

A feedback control application of the present invention entails using a function to predict real-time blood glucose levels, or measurement values of blood glucose levels at a different time, and then the same to control a pump for insulin delivery to treat hyperglycemia.

EXAMPLES

The following examples are put forth so as to provide those of ordinary skill in the art with a complete disclosure and description of how to make and use the devices, methods, and formulae of the present invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Signal Processing for Measurement of Blood Glucose

In order to assess the signal processing methods of the present invention, an iontophoretic sampling device was used to extract a series of 525 blood glucose samples from an experimental population of human subjects, and non-processed measurement values were compared against measurement values obtained using the data screening and correction algorithm of the present invention.

More particularly, iontophoretic sampling was performed on subjects using a GlucoWatch™ (Cygnus, Inc., Redwood City, Calif.) iontophoretic sampling system. This transdermal sampling device, which is designed to be worn like a wrist watch, uses iontophoresis (electroosmosis) to extract glucose analyte into a collection pad worn beneath the watch. Glucose collected into the GlucoWatch™ sampling system triggers an electrochemical reaction with a reagent in the pad, giving rise to a current which is sensed, measured, and converted to a blood glucose concentration. Measurements are taken on a continual basis, wherein combined extraction and sensing (measurement cycles) were set at 30 minutes. Iontophoresis was carried out using two collection pads contacted with Ag/AgCl iontophoretic electrodes, an iontophoretic current density of 0.3 mA/cm$^2$, and the electrical polarity of the electrodes was switched halfway through the 30 minute measurement cycle. Sensing was carried out using platinum-based biosensor electrodes which were contacted with the collection pads. A description of the GlucoWatch™ sampling system can be found in publication to Conn, T. E. (Jan. 15, 1997) *"Evaluation of a Non-Invasive Glucose Monitoring System for People with Diabetes,"* given at the Institute of Electrical and Electronics Engineers (IEEE) meeting entitled "Engineering in Medicine & Biology," Stanford, Calif., which publication is incorporated herein by reference.

Concurrent with obtaining the calculated blood glucose values (from the GlucoWatch™ sampling system), blood samples (finger sticks) were obtained and analyzed for use as reference measurements. As a result, 525 sets of paired measurements (reference and calculated measurements) were obtained. A comparison was then made between the reference measurements and the calculated measurements (either raw, or signal processed using the methods of the invention). Two different sets of data screens were used as follows: (a) maximum temperature change over time (d(temp)/d(time)), perspiration threshold, and a threshold departure from monotonicity (this set of temperature screens is indicated as (+) in Table 1 below); or (b) maximum temperature change over time (d(temp)/d(time)), perspiration threshold, a threshold departure from monotonicity, and a threshold baseline background change over time (this set of temperature screens is indicated as (++) in Table 1 below). The correction algorithm that was used is as follows:

$$EG_t = b_{gain}[E_t(1+\epsilon_i t)+OS] + \alpha_i t - \rho$$

wherein:

$$b_{gain} = \frac{BG_{cal} + \rho - \alpha_{cal} t}{E_{cal}(1 + \epsilon_i t_{cal}) + OS}$$

and ($t_{cal}$) is the calibration point; ($EG_t$) is the estimated blood glucose concentration at time t; ($E_t$) is the analyte signal at time t; (OS) is the constant offset term which accounts for a non-zero signal at an estimated zero blood glucose concentration (as described above); ($\epsilon$) is a gain term for time-dependent signal decline and can have multiple time segments (e.g., i=1, 2, or 3); ($\alpha$) is a correction term for a linear time-dependent signal decline in the time segments and can have multiple time segments (e.g., i=1, 2, or 3); (t) is the elapsed time, and ($\rho$) is the calibration offset (in mg/dl).

In the comparison, an Error Grid Analysis (Clarke et al. (1987) *Diabetes Care* 10:622–628) was used to assess device effectiveness, wherein calculated measurements were plotted against the corresponding reference measurements. An effective blood glucose monitoring device should have greater than approximately 85–90% of the data in the A and B regions of the Error Grid Analysis, with a majority of the data in the A region (Clark et al., supra). The results of the Error Grid Analysis are presented below in Table 1 as (A+B%). As can be seen, the combination of data screening methods and the correction algorithm of the present invention met this effective criteria.

Another measure of device accuracy is the mean absolute % error (MPE(%)) which is determined from the mean of individual % error (PE) given by the following function:

$$PE = \frac{EG_t - BG_t}{BG_t}$$

wherein $BG_t$ is the reference glucose measurement and $EG_t$ is the calculated glucose measurement. Effective measurements should have a MPE(%) of about 25% or less. The results of the MPE(%) are also depicted in Table 1. As can be seen, the combination of data screening methods and the correction algorithm of the present invention met this effective criteria.

The correlation between calculated and measured blood glucose values was also assessed. The correlation coefficient values (R) are also presented in Table 1 below. Effective measurements should have R values of greater than about 0.85. As can be seen, the combination of data screening methods and the correction algorithm of the present invention provide for increased correlation between actual and measured values.

TABLE 1

| | | 525 Total Paired Data | | | | |
|---|---|---|---|---|---|---|
| Algorithm | Screen | No. pts. | MPE (%) | A + B (%) | Other (%) | R |
| 0 | 0 | 525 | 54 | 73 | 27 | 0.54 |
| + | + | 467 | 24 | 90 | 10 | 0.87 |
| + | ++ | 308 | 20 | 91 | 9 | 0.90 |

What is claimed is:

1. A method for measuring an analyte present in a biological system, said method comprising:
   (a) transdermally extracting the analyte from the biological system using a sampling system that is in operative contact with a skin or mucosal surface of said biological system;
   (b) obtaining a raw signal from the extracted analyte, wherein said raw signal is related to analyte concentration;
   (c) subjecting the raw signal obtained in step (b) to a conversion step in order to convert said raw signal to an initial signal output which is indicative of the amount of analyte extracted by the sampling system;
   (d) performing a calibration step which converts the initial signal output obtained in step (c) to a measurement value indicative of the concentration of analyte present in the biological system at the time of extraction; and
   (e) repeating steps (a)–(c) at least once to obtain a plurality of measurement values, wherein the sampling system is maintained in operative contact with the skin or mucosal surface of said biological system to provide for analyte measurement.

2. The method of claim 1, wherein the analyte is extracted from the biological system into a first collection reservoir to obtain a concentration of the analyte in said reservoir.

3. The method of claim 2, wherein the first collection reservoir is in contact with the skin or mucosal surface of the biological system and the analyte is extracted using an iontophoretic current applied to said skin or mucosal surface.

4. The method of claim 2, wherein the first collection reservoir contains an enzyme that reacts with the extracted analyte to produce an electrochemically detectable signal.

5. The method of claim 4, wherein the analyte is glucose and the enzyme is glucose oxidase.

6. The method of claim 1, wherein the raw signal obtained in step (b) is subjected to a data screen which invalidates or corrects poor or incorrect signals based on a detected parameter indicative of a poor or incorrect signal.

7. The method of claim 6, wherein the data screen applies a set of selection criteria to the raw signal, wherein each selection criterium is based on a different detected parameter indicative of a poor or incorrect signal.

8. The method of claim 6, wherein the data screen entails monitoring changes in temperature over time during steps (a) and (b), and a maximum temperature change over time (d(temp)/d(time)) value is used to invalidate or correct measurements taken during a measurement period during which the maximum d(temp)/d(time) value was exceeded.

9. The method of claim 6, wherein the data screen entails monitoring perspiration levels in the biological system at selected time points, and a maximum perspiration level threshold is used to invalidate or correct measurements taken during a measurement period during which the maximum perspiration level threshold was exceeded.

10. The method of claim 3, wherein the raw data obtained in step (b) is subjected to a data screen which entails monitoring iontophoretic voltage during steps (a) and (b), and uses a maximum iontophoretic voltage value to invalidate or correct measurements taken during a measurement period during which said maximum voltage value was exceeded.

11. The method of claim 1, wherein the conversion step entails a baseline background subtraction method to remove background noise from the raw signal.

12. The method of claim 11, wherein the baseline background subtraction method uses a temperature-corrected baseline value.

13. The method of claim 11, wherein the baseline background subtraction method uses a skin conductivity-corrected baseline value.

14. The method of claim 2, wherein the sampling system further comprises a second collection reservoir which does not contain the enzyme, and step (b) further entails obtaining a blank signal from said second collection reservoir, which blank signal is used in step (c) as a blank correction value to remove background information from the initial signal output.

15. The method of claim 2, wherein the sampling system further comprises a second collection reservoir containing an enzyme that reacts with the extracted analyte to produce an electrochemically detectable signal, and step (b) further entails obtaining signals from said first and second collection reservoirs.

16. The method of claim 1, wherein the conversion step integrates the initial signal output over a sensing time period.

17. The method of claim 14, wherein the conversion step uses a mathematical transformation to individually smooth the signals obtained from the first and second collection reservoirs.

18. The method of claim 15, wherein the conversion step uses a mathematical transformation to individually smooth the signals obtained from the first and second collection reservoirs.

19. The method of claim 17, wherein the difference between signals obtained from the first and second collection reservoirs are smoothed.

20. The method of claim 1, wherein the calibration step entails a single-point calibration against a calibration reference value.

21. The method of claim 1, wherein the calibration step entails the use of a neural network algorithm that correlates the initial signal output obtained in step (c) with a measurement value indicative of the concentration of analyte present in the biological system at the time of extraction.

22. The method of claim 1, wherein the sampling system is programmed to begin obtaining raw signal at a designated time.

23. The method of claim 22, wherein the designated time precedes step (d).

24. The method of claim 1, wherein the calibration step entails the use of a linear correlation to correlate the initial signal output obtained in step (c) with a measurement value indicative of the concentration of analyte present in the biological system at the time of extraction.

25. The method of claim 1, wherein the calibration step further entails compensating for time-dependent behavior between signal measurements obtained in step (b).

26. The method of claim 25, wherein the time-dependent behavior comprises signal decline between said measurements.

27. The method of claim 25, wherein the compensating is carried out using the following function:

$$EG_t = \left(\left[\frac{BG_{cal} - \alpha t_{cal}}{E_{cal} + OS} - \gamma t_{cal}\right] + \gamma t\right) * (E_t + OS) + \alpha t$$

where $BGAIN = \left[\frac{BG_{cal} - \alpha t_{cal}}{E_{cal} + OS} - \gamma t_{cal}\right]$ wherein: $BG_{cal}$ is the true blood glucose at the calibration point; $E_{cal}$ is the analyte signal at calibration; ($t_{cal}$) is the elapsed time of the calibration point; ($EG_t$) is the estimated blood glucose concentration at time t; ($E_t$) is the analyte signal at time t; (OS) is the constant offset term which accounts for a non-zero signal at an estimated zero blood glucose concentration; ($\gamma$) is a time-dependent correction term for signal decline; ($\alpha$) is a time-dependent correction term for signal decline; and (t) is the elapsed time.

28. The method of claim 27, wherein a time segmentation is performed as follows:

$$BGAIN_1 = \left[\frac{BG_{cal} - \alpha_1 t_{cal}}{E_{cal} + OS} - \gamma_1 t_{cal}\right] \text{ if } t < t_{12}$$

$$BGAIN_2 = \left[\frac{BG_{cal} - \alpha_1 t_{12} - \alpha_2(t_{cal} - t_{12})}{E_{cal} + OS} - \gamma_1 t_{12} - \gamma_2(t_{cal} - t_{12})\right]$$

if $t_{12} < t_{cal} < t_{23}$ $$BGAIN_3 = \left[\frac{BG_{cal} - \alpha_1 t_{12} - \alpha 2(t_{cal} - t_{12}) - \alpha 3(t_{cal} - t_{23})}{E_{cal} + OS} - \right.$$

$$\left. \gamma_1 t_{12} - \gamma_2(t_{cal} - t_{12}) - \gamma_3(t_{cal} - t_{23})\right]$$

if $t_{23} < t_{cal}$ $EG_t = (BGAIN_1 + \gamma_1 t)*(E_t + OS) + \alpha_1 t$ if $t < t_{12}$ $EG_t = (BGAIN_2 + \gamma_1 t_{12} + \gamma_2(t - t_{12}))*(E_t + OS) + \alpha_1 t_{12} + \alpha_2(t - t_{12})$ if $t_{12} < t < t_{23}$ $$EG_t = (BGAIN_3 + \gamma_1 t_{12} + \gamma_2(t_{23}-t_{12}) + \gamma_3(t-t_{23}))*(E_t + OS) + \alpha_1 t_{12} + \alpha_2(t_{23}-t_{12}) + \alpha_3(t-t_{23})$$

if $t_{23} < t$ wherein: $EG_t$ is the calculated value of blood glucose at the measurement time; $BG_{cal}$ is the true blood glucose at the calibration point, t is the elapsed time; $t_{cal}$ is the elapsed time at the calibration point; OS is the offset parameter; and $\alpha_i$ and $\gamma_i$ are time dependent correction terms to account for declining signal with time, where i=1, 2, or 3.

29. The method of claim 1, wherein the conversion step further entails using a temperature correction function to correct for changes in the biological system and/or changes in the sensing device.

30. The method of claim 29, wherein the changes in the biological system comprise a change in temperature.

31. The method of claim 29, wherein the conversion step entails correcting for temperature changes occurring between a measurement of background signal in the sensing device and measurement of a raw signal in step (b), and during the measurement of the raw signal.

32. The method of claim 31, wherein the temperature correction uses an Arrhenius correction function.

33. The method of claim 31, wherein the temperature correction uses an integral average temperature correction function obtained from a measurement cycle to correct for temperature at subsequent time points.

34. The method of claim 29, wherein the conversion step entails correcting for temperature differences between multiple signals obtained from the sensing device.

35. The method of claim 2, wherein said biological system includes skin, and said extracting of analyte from the biological system into a reservoir further comprises enhancement of skin permeability by pricking the skin with microneedles.

36. A monitoring system for measuring an analyte present in a biological system, said system comprising, in operative combination:
   (a) sampling means for extracting the analyte from the biological system, wherein said sampling means is adapted for extracting the analyte across a skin or mucosal surface of said biological system;
   (b) sensing means in operative contact with the analyte extracted by the sampling means, wherein said sensing means obtains a raw signal from the extracted analyte and said raw signal is specifically related to the analyte; and
   (c) microprocessor means in operative communication with the sensing means, wherein said microprocessor means (i) subjects the raw signal to a conversion step to convert said raw signal to an initial signal output which is indicative of the amount of analyte extracted by the sampling means, and (ii) performs a calibration step which correlates said initial signal output with a measurement value indicative of the concentration of analyte present in the biological system at the time of extraction.

37. The monitoring system of claim 36, wherein the sampling means includes one or more collection reservoirs for containing the extracted analyte.

38. The monitoring system of claim 37, wherein the sampling means uses an iontophoretic current to extract the analyte from the biological system.

39. The monitoring system of claim 38, wherein the collection reservoir contains an enzyme that reacts with the extracted analyte to produce an electrochemically detectable signal.

40. The monitoring system of claim 39, wherein the analyte is glucose and the enzyme is glucose oxidase.

41. The monitoring system of claim 36 further comprising temperature sensing means and skin conductance sensing means for monitoring temperature and skin conductance in the monitoring system or biological system.

42. The monitoring system of claim 36, wherein the microprocessor is programed to begin execution of sampling and sensing at a defined time.

43. A monitoring system for measuring an analyte present in a biological system, said system comprising,
   one or more microprocessors capable of (i) subjecting a raw signal, obtained from an extracted analyte, to a conversion step to convert said raw signal to an initial signal output which is indicative of an amount or concentration of the extracted analyte, and (ii) performing a calibration step which correlates said initial signal output with a measurement value indicative of the amount or concentration of analyte present in the biological system at the time of analyte extraction.

44. The method of claim 25, wherein the compensating is carried out using the following function:

$$EG_t = b_{gain}[E_t(1+\epsilon_i t) + OS] + \alpha_i t - \rho$$

wherein:

$$b_{gain} = \frac{BG_{cal} + \rho - \alpha_i t_{cal}}{E_{cal}(1 + \epsilon_i t_{cal}) + OS}$$

and ($t_{cal}$) is the calibration point; ($EG_t$) is the estimated blood glucose concentration at time t; ($E_t$) is the analyte signal at time t; (OS) is the constant offset term which accounts for a non-zero signal at an estimated zero blood glucose concentration; ($\epsilon$) is a gain term for time-dependent signal decline and can have multiple time segments; (i) is a time segment; ($\alpha$) is a correction term for a linear time-dependent signal decline in the time segments and can have multiple time segments; (t) is the elapsed time, ($BG_{cal}$) is the true blood glucose at the calibration point; ($E_{cal}$) is the analyte signal at calibration; and ($\rho$) is the calibration offset.

* * * * *

UNITED STATES PATENT AND TRADEMARK OFFICE
CERTIFICATE OF CORRECTION

PATENT NO. : 6,233,471 B1  Page 1 of 1
DATED : May 15, 2001
INVENTOR(S) : Bret Berner et al.

It is certified that error appears in the above-identified patent and that said Letters Patent is hereby corrected as shown below:

Title page,
Title "SIGNAL PROCESSING FOR MEASUREMENT OF PHYSIOLOGICAL ANALYSIS" should be --SIGNAL PROCESSING FOR MEASUREMENT OF PHYSIOLOGICAL ANALYTES --.

Signed and Sealed this

Eighth Day of January, 2002

Attest:

JAMES E. ROGAN
Attesting Officer  Director of the United States Patent and Trademark Office